United States Patent [19]

Milstein

[11] Patent Number: 4,581,178
[45] Date of Patent: Apr. 8, 1986

[54] ADDITION OF ALDEHYDES TO ORGANIC COMPOUNDS HAVING A CARBON-HYDROGEN BOND ACTIVATED BY A NITRO OR NITRILE GROUP

[75] Inventor: David Milstein, Wilmington, Del.

[73] Assignee: E. I. Du Pont de Nemours and Company, Wilmington, Del.

[21] Appl. No.: 707,017

[22] Filed: Feb. 28, 1985

[51] Int. Cl.$^4$ .............. C07C 121/75; C07C 121/34; C07C 79/18; C07C 79/22
[52] U.S. Cl. .................................... 558/409; 568/705; 568/709; 568/710; 568/711; 568/712; 568/713; 544/49; 544/215; 546/176; 546/180; 546/246; 546/330; 546/334; 548/205; 548/341; 548/503; 548/561; 548/566; 549/58; 549/75; 549/467; 549/491; 562/434; 562/437; 562/438; 562/561; 562/567; 564/87; 564/95; 564/96; 564/441; 564/503; 568/704
[58] Field of Search ............ 260/465 F, 465.6, 465 D, 260/465 E, 465.4, 465.5; 568/704, 705, 709, 710-713; 546/334; 562/434, 437, 438, 561, 567; 564/87, 95, 96, 441, 503

[56] References Cited

U.S. PATENT DOCUMENTS 3,564,062  2/1971  Tindall ........................... 568/704 X
3,723,546  3/1973  Bachman et al. .............. 568/704 X

OTHER PUBLICATIONS

Cope et al., eds. *Organic Reactions*, vol. 15, pp. 204-273 (Wiley, New York, 1967).
Baer et al., "Activating and Directing Effects of the Nitro Group in Aliphatic Systems", in Feuer et al., Eds., *The Chemistry of the Nitro and Nitroso Groups*, pp. 75-187 (Wiley-Interscience, New York, 1970).
Iwata et al., *Bull. Chem. Soc. Jpn.* 49:1369 (1976).
Irie et al., *Bull. Chem. Soc. Jpn.* 53:1366 (1980).
Irie et al., *Bull. Chem. Soc. Jpn.* 54:1195 (1981).
Watanabe et al., *Bull. Chem. Soc. Jpn.* 55:3208 (1982).
Irie, *Nippon Kagaku Kaishi* 1983(1):150 (1983) (CA 98:160318m).

*Primary Examiner*—Dolph H. Torrence

[57] ABSTRACT

Low valent transition metal complexes containing small cone angle phosphine or arsine ligands efficiently catalyze addition of aldehydes to compounds or groups having a C—H bond activated by a nitro or nitrile group, to provide nitroalcohols or cyanohydrins, respectively.

13 Claims, No Drawings

ADDITION OF ALDEHYDES TO ORGANIC COMPOUNDS HAVING A CARBON-HYDROGEN BOND ACTIVATED BY A NITRO OR NITRILE GROUP

BACKGROUND OF THE INVENTION

The present invention relates generally to synthetic organic chemistry, and particularly to a process for adding aldehydes to certain organic compounds having active C—H bonds.

Base-catalyzed reaction of aldehydes or ketones with compounds having active methylene groups is a widely employed reaction commonly known as the Knoevenagel condensation. Activation of the methylene group is brought about by attachment of a group such as nitro, cyano, or acyl. In most cases, two such groups are required to provide sufficient activation. The primary product is typically an unsaturated compound resulting from combination of starting materials, followed by dehydration. The primary product can undergo a Michael addition reaction with a second molecule of the active methylene compound to provide a bis compound. Variations of the Knoevenagel condensation are discussed by Jones, "The Knoevenagel Condensation", in Cope et al., eds., *Organic Reactions* Vol. 15, pp. 204–273, (Wiley, New York, 1967).

A special case of the Knoevenagel reaction is the Henry addition, which involves base-catalyzed combination of an aldehyde or ketone and a nitroalkane. This reaction is discussed by Baer et al., "Activating and Directing Effects of the Nitro Group in Aliphatic Systems", in Feuer et al., eds., *The Chemistry of the Nitro and Nitroso Groups*, pp. 75–187, (Wiley-Interscience, New York, 1970).

A number of workers have disclosed aldol condensations of aldehydes and ketones catalyzed by transition metal complexes. As used herein, "condensation" refers to a reaction wherein addition is followed by dehydration.

Iwata et al., *Bull. Chem. Soc. Jpn.* 49:1369 (1976), disclose aldol condensations of aromatic and aliphatic aldehydes with ketones in the presence of Cu(II) ion.

Irie et al., *Bull. Chem. Soc. Jpn.* 53:1366 (1980), disclose aldol condensations of aldehydes with ketones, catalyzed by transition metal(II) complexes, to provide α,β-unsaturated ketones. Specifically, Irie et al. report use of complexes of Co(II), Ni(II), Cu(II), and Zn(II) acetates with 2,2'-bipyridine as catalysts in these reactions, which were conducted at 80° C. in dimethylformamide.

Irie et al., *Bull. Chem. Soc. Jpn.* 54:1195 (1981), describe condensations of benzaldehyde with acetophenone, using a Co(II) acetate-2,2'-bipyridine catalyst complex in dimethylformamide.

Watanabe et al., *Bull. Chem. Soc. Jpn.* 55:3208 (1982), disclose aldol condensation reactions catalyzed by Co(II) complexes of pyridine-containing copolymers. Watanabe et al. note that use of dimethylformamide or dimethyl sulfoxide as solvent is required in these reactions, and that condensations involving aliphatic aldehydes and ketones did not proceed as successfully as those involving aromatic compounds.

Irie, *Nippon Kagaku Kaishi* 1983(1):150 (1983) (CA 98:160318m), describes addition of certain aromatic aldehydes to nitromethane in the presence of a Ni(II)-2,2'-bipyridine complex to provide aromatic nitroalcohols. In this case, addition was not followed by dehydration. Dimethylformamide was employed as solvent.

It has now been found that addition of aldehydes to compounds having active C—H bonds can be efficiently catalyzed under neutral conditions by electron-rich, low valent transition metal complexes containing small cone angle phosphine or arsine ligands. This reaction provides alcohols in high yields, primarily without continuation to provide dehydration products. In addition, the reaction of the present invention is quite sensitive to catalyst steric hindrance, enabling avoidance of further combination of initial products with aldehyde starting materials. The reaction provided herein can be conducted with equimolar quantities of reactants, and is not limited to particular solvent systems.

SUMMARY OF THE INVENTION

The present invention provides a catalytic process for preparing nitroalcohols or cyanohydrins, comprising reacting an aldehyde compound or group of formula $$RCHO \qquad (I)$$

with a compound or group of formula

(II)

(III)

in the presence of a catalytic amount of a low-valent transition metal complex selected from the group consisting of (a)

$$M^1A_nB_mX; \qquad (IV)$$

(b)

$$M^2A_jB_k; \qquad (V)$$

(c)

$$M^3A_sB_t; \text{ and} \qquad (VI)$$

(d) precursors which are converted to complexes of formulas IV, V, or VI during the process;

wherein

A is a phosphine or arsine ligand moiety having a ligand cone angle $\theta$ which is less than or equal to 132°, selected from the group consisting of $$ER^5R^6R^7, \qquad (VII)$$

$$[R^8R^9E(CH_2)_pER^{10}R^{11}]/2, \text{ or} \qquad (VIII)$$

mixtures thereof;

B is an olefin, or a phosphine or arsine ligand moiety A', defined as A, above, except that $\theta$ can be greater than 132°;

E is P or As;

$M^1$ is Co(I), Rh(I), or Ir(I);

$M^2$ is Ni(O), Pd(O), or Pt(O);

$M^3$ is Fe(O), Ru(O) or Os(O);

R is hydrogen, or a hydrocarbyl radical which is alkyl, substituted alkyl, aryl, substituted aryl, aralkyl, substituted aralkyl, alkaryl, substituted alkaryl, or heterocyclic;

$R^1$, $R^2$ and $R^4$ are, independently, F, $NO_2$, COR, COOR, CN, or R;

$R^3$ is F, $NO_2$, CN or RCH=CH;

$R^5$, $R^6$, $R^7$, $R^8$, $R^9$, $R^{10}$, and $R^{11}$ are, independently, hydrogen, lower alkyl, or lower aryl;

X is an anion;

j is 2, 3, or 4;

k, m, and t are independently 0 or 1;

n is 2, 3, 4, or 5;

p is 1, 2, or 3; and s is 3, 4 or 5;

provided that the sum of m and n is less than or equal to 5, the sum of j and k is less than or equal to 4, and the sum of s and t is less than or equal to 5.

DETAILED DESCRIPTION OF THE INVENTION

The present invention provides a process for adding aldehydes to compounds containing C—H bonds activated by the presence of nitro or cyano groups. This process can be described by the following formulas:

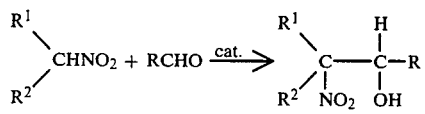

and

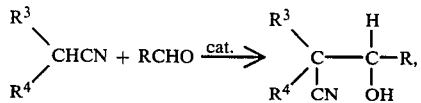

$R^1$, $R^2$, $R^3$ and $R^4$ in the foregoing formulas are as previously defined, and the catalyst employed is a low-valent transition metal complex containing small cone angle phosphine or arsine ligands. Where nitriles comprising terminal unsaturated carbons are employed as reactants, products are typically provided as a mixture of isomers. The process of the present invention comprises intramolecular reactions as well as reactions of separate starting materials. Thus, the groups identified by Formulas I, II, and III, above, can be separate parts of the same molecule.

NOMENCLATURE

As used throughout the specification, either individually or as part of a larger group, "alkyl" means a linear, cyclic, or branched-chain aliphatic radical of 1 to 20 carbon atoms, which can be saturated or unsaturated; "lower alkyl" means an alkyl group of 1 to 6 carbon atoms. "Substituted alkyl" and "substituted lower alkyl" mean alkyl and lower alkyl groups, respectively, substituted with one or more nitro, alkoxy, halo, amino, carboxy, cyano, thio, or sulfonamido groups, and optionally containing a in-chain heteroatom or heteroatoms such as N, O, or S. "Aryl" means an aromatic radical, e.g., phenyl, of 6 to 30 carbon atoms, and "substituted aryl" means aryl substituted with one or more alkyl, substituted alkyl, nitro, alkoxy, halo, amino, cyano, carboxy, thio or sulfonamido groups. However, in selection of reactants, substituted molecules capable of deactivating catalyst should be avoided or reacted in a non-deactivating form. "Lower aryl" means aryl of 6 to 10 carbons. "Aralkyl" means a linear or branched-chain aliphatic radical of 7 to 30 carbon atoms comprising an aryl group or groups. "Alkaryl" means an aryl radical of 7 to 30 carbons having one or more aliphatic substituents. As used herein, "halo" means F, Cl, Br or I; and "heterocyclic" means a cycloalkyl or aryl radical comprising one or more cyclic moieties, wherein at least one such moiety comprises a heteroatom selected from the group consisting of N, O or S. "Olefin" means an alkyl radical comprising at least two unsaturated carbons.

Examples of alkyl groups or radicals include methyl, ethyl, propyl, butyl, pentyl, hexyl, heptyl, octyl, nonyl, decyl, undecyl and dodecyl, as well as isomeric or unsaturated forms thereof. Examples of cyclic alkyl groups include cyclopropyl, cyclobutyl, cyclopentyl, cyclohexyl, 2-methylcyclopropyl, 2,2-dimethylcyclopropyl, 3-propylcyclobutyl, 2,3,4-triethylcyclobutyl, cycloheptyl, cyclooctyl, and cyclononyl.

Examples of aryl radicals include phenyl, naphthyl, and anthracyl. Examples of aralkyl groups include benzyl, 2-phenylethyl, and 3-phenylbutyl. Examples of alkaryl groups include tolyl, ethylphenyl, methylphenyl, and xylyl. Exemplary heterocyclic radicals include furyl, pyridyl, thienyl, indolyl, benzthienyl, phthalidyl, piperidino, benzodiazinyl, benzothiazinyl, coumaryl, quinolyl, imidazolyl, thiazolyl, pyrrolyl, pyrrolidinyl, and triazinyl.

The following abbreviations are employed in the specification:

| | |
|---|---|
| i-Bu | isobutyl |
| s-Bu | sec-butyl |
| t-Bu | tert-butyl |
| Bz | benzyl |
| Cy | cyclohexyl |
| Et | ethyl |
| Me | methyl |
| Ph | phenyl |
| i-Pr | isopropyl |
| n-Pr | n-propyl |
| To | tolyl |

As used herein, "anion" means a negatively charged atom or radical, coordinating or noncoordinating. Examples of coordinating anions include $Cl^-$, $Br^-$, $I^-$, $F^-$, $RCOO^-$, $OH^-$, $NO_3^-$, $SO_4^{2-}$, and $PO_4^{3-}$. Examples of noncoordinating anions include $PF_6^-$, $B(C_6H_5)_4^-$, $BF_4^-$, $SbF_6^-$, $ClO_4^-$, and $CF_3SO_3^-$.

Preferred values for R, $R^1$, $R^2$, and $R^4$ are H, lower alkyl, lower alkaryl, and lower aryl. Preferred values for $R^3$ are RCH=CH, where R is H, lower alkyl, lower alkaryl, and lower aryl, and CN. Particularly preferred values for R, $R^1$, $R^2$ and $R^4$ are H and lower alkyl. A particularly preferred value for $R^3$ is RCH=CH, where R is H or lower alkyl.

CATALYST SELECTION

The catalysts employed in the process of the present invention are low valent transition metal complexes of Co(I), Rh(I), Ir(I), Ni(O), Pd(O), Pt(O), Fe(O), Ru(O), and Os(O), comprising small cone angle phosphine and/or arsine ligands. These catalysts can be described by reference to the following formulas:

(a)

$$M^1A_nB_mX; \qquad (IV)$$

(b)

$$M^2A_jB_k; \text{ and} \qquad (V)$$

(c)

$$M^3A_sB_t. \qquad (VI)$$

In addition, the process of the present invention can be practiced by adding precursors of the foregoing catalyst complexes to reaction mixtures, such that catalysts of formulas IV, V, or VI are produced in situ under process conditions.

In the foregoing formula IV, $M^1$ is Co, Rh, or Ir; A is a phosphine or arsine ligand moiety, detailed below; B is an olefin, or a phosphine or arsine ligand moiety A', which is not subject to the ligand cone angle restriction applicable to moiety A. X is an anion, m is 0 or 1; and n is 2, 3, 4, or 5, provided that the sum of m and n is less than or equal to 5.

In the foregoing formula V, $M^2$ is Ni, Pd, or Pt; and A and B are as defined above. Integer j and k is 2, 3, or 4; and integer k is 0 or 1, provided that the sum of j and k is less than or equal to 4.

In the foregoing formula VI, $M^3$ is Fe, Ru, or Os; and A and B are as defined above. Integer s is 3, 4 or 5, and integer t is 0 or 1, provided that the sum of s and t is less than or equal to 5.

In formulas IV, V, and VI, ligand species A is a phosphine or arsine ligand moiety subject to a ligand cone angle restriction. Ligand cone angle is specified by a steric parameter $\theta$, and is reported in degrees. This parameter is discussed in detail by Tolman, "Steric Effects of Phosphorus Ligands in Organometallic Chemistry and Homogenous Catalysis", *Chemical Reviews* 77, pp. 314–348 (1977). The disclosure of this review article is incorporated by reference herein. As noted by Tolman, $\theta$ for a given symmetric P ligand corresponds to the apex angle of a cylindrical cone, which is centered 2.28 Å (2.57 nm) from the center of a P atom at the center of the ligand group, and which just touches the van der Waals radii of the outermost atoms of the ligand group. If there are internal degrees of freedom, i.e., rotation about P—C bonds, substituents are folded back to provide a minimum cone angle. Cone angles can be determined for unsymmetrical ligands $PR^5R^6R^7$ by using a model to minimize the sum of half angles ($\theta_i/2$) in the following equation:

$$\theta = (\tfrac{2}{3}) \sum_{i=1}^{3} \theta_i/2$$

As previously noted, $\theta$ for the phosphine or arsine ligands A in catalyst complexes emloyed in the process of the present invention must be less than or equal to 132°. The Tolman review cited above notes, at p. 340, that ligands containing As can be expected to exhibit values for $\theta$ which are slightly less than values for corresponding phosphorus ligands. Thus, known values for analogous phosphorus ligands, where available, can be employed to distinguish As ligands within the scope of the 132° cone angle restriction. The following Table 1, which is derived from the review cited above, lists values of $\theta$ for a number of phosphorus ligands:

TABLE 1

Values of Steric Parameter $\theta$ for Common Phosphorus Ligands

| Ligand Type | | | |
|---|---|---|---|
| $PX_3$ | $PR_3$ | Other | $\theta$, degrees |
| $PH_3$ | | | 87 |
| | | $PH_2Ph$ | 101 |
| | | $Me_2PCH_2CH_2PMe_2$ | 107 |
| $P(NCH_2CH_3)_3$ | | | 108 |
| | | $Et_2PCH_2CH_2PEt_2$ | 115 |
| | $PMe_3$ | | 118 |
| | | $Ph_2PCH_2PPh_2$ | 121 |
| | | $PMe_2Ph$ | 122 |
| | | $Ph_2P(CH_2)_2PPh_2$ | 125 |
| | | $Ph_2P(CH_2)_3PPh_2$ | 127 |
| | | $PHPh_2$ | 128 |

Exemplary catalyst complexes useful in various processes of the present invention include low-valent transition metal complexes (Co(I), Rh(I), Ir(I), Ni(O), Pd(O), Pt(O), Fe(O), Ru(O), or Os(O)) with the phosphine ligand moieties set forth below. Replacement of the phosphorus atom by an arsenic atom in the following ligands provides arsine ligand complexes within the scope of catalysts useful in the processes of the present invention. The following ligands correspond to formulas VII ($ER^5R^6R^7$) and VIII ($R^8R^9E(CH_2)_pPR^{10}R^{11})/2$ set forth above.

| $PR^5R^6R^7$ | | (VII) |
|---|---|---|
| $PMe_3$ | trimethylphosphine | |
| $PEt_3$ | triethylphosphine | |
| $P(i-Pr)_3$ | triisopropylphosphine | |
| $P(n-Bu)_3$ | tributylphosphine | |
| $PH_2Ph$ | phenylphosphine | |
| $PHPh_2$ | diphenylphosphine | |
| $R^8R^9P(CH_2)_pPR^{10}R^{11}$ | | (VIII × 2) |
| dmpe | $[(CH_3)_2PCH_2CH_2P(CH_3)_2]$ | |
| | 1,2-ethanediylbis(dimethylphosphine) | |
| depe | $[(C_2H_5)_2PCH_2CH_2P(C_2H_5)_2]$ | |
| | 1,2-ethanediylbis(diethylphosphine) | |
| dppm | $[Ph_2PCH_2PPh_2]$ | |
| | methylenebis(diphenylphosphine) | |
| dppe | $[Ph_2PCH_2CH_2PPh_2]$ | |
| | 1,2-ethanediylbis(diphenylphosphine) | |
| dppp | $[Ph_2PCH_2CH_2CH_2PPh_2]$ | |
| | 1,3-propanediylbis(diphenylphosphine) | |

Methods of preparing preferred catalyst complexes for use in the present invention can be found in the following articles, the relevant disclosures of which are herein incorporated by reference:

1. Chlorotris(trimethylphosphine)rhodium: $Rh(PMe_3)Cl$

Jones, R. A. et al, *J. Chem. Soc. Dalton Trans.* 511 (1980).

2. Chlorobis(trimethylphosphine)(triphenylphosphine)-rhodium: $Rh(PMe_3)_2(PPh_3)Cl$ Jones, R. A. et al., *J. Chem. Soc. Dalton Trans.* 511 (1980).

3. Chlorobis(1,2-ethanediylbis[dimethylphosphine])-rhodium: $Rh(dmpe)_2Cl$

Butler, S. A., and Chatt, J., *J. Chem. Soc. A.* 1970, 1411.

4. Chlorobis(1,2-ethanediylbis-[dimethylphosphine])-iridium: $Ir(dmpe)_2Cl$

Herskovitz, T., *Inorg. Syn.* 21:99 (1982).

5. Chloro(1,2-cyclooctene)tris(trimethylphosphine)-iridium: $(C_8H_{14}Ir(PMe_3)_3Cl$ Herskovitz, T., *Inorg. Syn.* 21:99 (1982).

6. Chlorotris(triethylphosphine)rhodium: $Rh(PEt_3)_3Cl$

Intille, G. M., *Inorg. Chem.* 11:695 (1972).
7. Tetrakis(trimethylphosphine)palladium: Pd(PMe₃)₄
   Kurau, W., and Musco, A., *Inorg. Chim. Acta.* 12: 187 (1975).

PROCESS CONDITIONS

Preferred catalyst concentrations for the process of the present invention range from about 0.01M to about 0.10M, although concentrations from 0.00001M to 1M can be employed.

The process of the present invention can be conducted within a broad range of temperatures and proceeds at atmospheric pressure. Temperatures from −40° C. to 150° C. are suitable, and temperatures from about 20° C. to about 80° C. are preferred. Preferably, the process of the present invention is run neat, in an inert atmosphere, e.g., nitrogen or argon.

Any inert common solvent, for example, aliphatic or aromatic hydrocarbons or ethers, is suitable. Preferably, the reaction process of the present invention is run neat when at least one of the reactants is a liquid at selected reaction temperature. Exemplary inert solvents include diethyl ether, pentane, hexane, cyclohexane, heptane, benzene, toluene, xylenes, and ethyl benzene.

Various reactant ratios are suitable for the process of the present invention, although approximately equimolar concentrations of reactants are preferred for simplicity. A slight excess of one reactant can be employed, or in the alternative, ratios ranging from 1:1000 to 1000:1.

INDUSTRIAL UTILITY

The process of the present invention can be applied to the synthesis of various specialty chemicals and pharmaceuticals.

BEST MODE

The best mode currently contemplated for conducting the process of the present invention is that illustrated by Examples 3 and 25, below.

In the following examples, all parts and percentages are by weight and all degrees are Celsius unless otherwise indicated. In the examples, "GC" refers to gas chromatography, "IR" to infrared spectroscopy, and "NMR" to nuclear magnetic resonance spectroscopy.

EXAMPLES 1–3

Reaction of Nitromethane and Acetaldehyde to Produce 2-Hydroxy-nitropropane

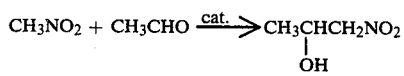

In Example 1, a 24 mL vial was charged with 1 mL (18.6 mmol) nitromethane, 1 mL (17.8 mmol) acetaldehyde, and 50 mg Rh(PMe₃)₃Cl in an N₂ dry box. The vial was capped, and the resulting reaction mixture was heated at 60° for about 18 hours. The vial was then opened and heated for an additional 15 minutes at 60° to remove residual acetaldehyde. Analysis by GC indicated loss of nitromethane and formation of a single product, which was isolated by preparative GC. NMR and IR confirmed that the resulting product was 2-hydroxy-nitropropane. The product mixture was distilled at 130° under water aspirator vacuum to yield 720 mg (6.9 mmol) of 2-hydroxy-nitropropane.

¹H NMR (CDCl₃) δppm: 1.30 (d, 3H, CH₃); 2.77 (broad s, 1H, OH); 4.22 (m, 3H, CH₂NO₂+CH—O).
IR (neat): 3380 (vs, broad, OH); 1550 (vs, NO₂).

In Example 2, a solution containing 0.5 g (8.2 mmol) nitromethane, 0.5 g (11.4 mmol) acetaldehyde, and 40 mg Rh(dmpe)₂Cl was stirred at 23°, under N₂, for 6 hours. IR and NMR of the resulting product mixture indicated quantitative conversion of nitromethane to 2-hydroxy-nitropropane.

In Example 3, 1.1 g (18.0 mmol) nitromethane were added to 50 mg Rh(dmpe)₂Cl and the resulting solution cooled to −30°. 0.81 g (18.4 mmol) acetaldehyde at 4° was added to form a reaction mixture, which was stirred at about 23° for 2 hours in a N₂ dry box. ¹H-NMR of the resulting product mixture indicated quantitative formation of product. Distillation in a Kugelrohr apparatus under water aspirator vacuum yielded 1.62 g (15.4 mmol, 85.5%) of product 2-hydroxy-nitropropane.

EXAMPLES 4–10 AND COMPARATIVE EXPERIMENTS A AND B

Effects of Catalyst Variation Upon Reaction of Nitromethane and Acetaldehyde to Produce 2-Hydroxy-nitropropane Examples 4–10 and Comparative Experiments A and B, which are summarized in Table II, below, were conducted substantially similarly to Example 1. Variations in catalysts or in reaction conditions are indicated in Table II.

TABLE II

| Example/<br>Comparative<br>Experiment | Catalyst | Conditions | Product<br>Yield<br>(%) |
|---|---|---|---|
| 4 | Rh(dmpe)₂Cl | 23°, 0.5 hr | >90 |
| 5 | Rh(PMe₃)₃Cl | 23°, 0.5 hr | >90 |
| 6 | Ir(dmpe)₂Cl | 23°, 0.5 hr | >90 |
| 7 | (C₈H₁₄)Ir(PMe₃)₃Cl | 23°, 0.5 hr | >90 |
| 8 | Ir(dmpe)₂Cl | 23°, 5 hr, in<br>0.8 M toluene | 50 |
| 9 | Ir(dmpe)₂Cl | 23°, 72 hr, in<br>0.8 M toluene | >99 |
| 10 | Rh(PEt₃)₃Cl | 23°, 0.5 hr | >90 |
| A | None | 60°, 18 hr | 0 |
| B | Rh(PPh₃)₃Cl | 60°, 18 hr | 0 |

EXAMPLES 11–13 AND COMPARATIVE EXPERIMENT C

Reaction of 1-Nitropropane and Acetaldehyde to Produce 2-Hydroxy-3-Nitropentane

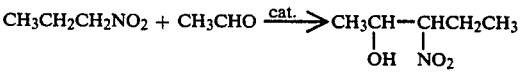

In each of Examples 11–13 and Comparative Experiment C, a 25 mL bottle was charged with 1.4 g (15.7 mmol) 1-nitropropane and 0.8 g (18.2 mmol) acetaldehyde in a N₂ dry box. After addition of the quantity of catalyst indicated below, the bottle was sealed and the resulting reaction allowed to proceed at 23°. At the times indicated, the bottle was sampled for analysis by IR. The catalysts employed and the results obtained are set forth in Table III, below.

TABLE III

| Example/Comparative Experiment | Catalyst | Quantity (mg) | Time | Product Yield (%) |
|---|---|---|---|---|
| 11 | Rh(PMe₃)₃Cl | 30 | 24 hr | >90 |
| 12 | Rh(dmpe)₂Cl | 40 | 5 min | >90 |
| 13 | Pd(PMe₃)₄ | 50 | 5 min | >90 |
| C | Pd(PCy₃)₂ | 70 | 18 hr | 0 |

EXAMPLES 14 AND 15

Reaction of Butyraldehyde and Nitromethane to Produce 2-hydroxy-nitropentane

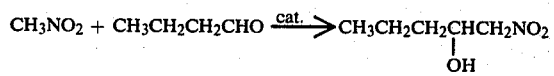

Example 14, 0.59 g (8.2 mmol) butyraldehyde, 0.50 g (8.2 mmol) nitromethane, and 25 mg Ir(dmpe)₂Cl were reacted at 23° for four hours in a sealed tube. IR analysis at the end of this period indicated formation of traces of 2-hydroxy-nitropentane.

In Example 15, 0.60 g (8.3 mmol) butyraldehyde, 0.50 g (8.2 mmol) nitromethane, and 50 mg Rh(PMe₃)₃Cl were reacted at 60° in a sealed tube for about 18 hours. IR and ¹H-NMR analysis at the end of this period indicated conversion of more than 90% of available starting materials to 3-hydroxy-nitropentane.

EXAMPLES 16 AND 17

Reaction of Nitromethane and Benzaldehyde to Produce 2-Hydroxynitroethylbenzene

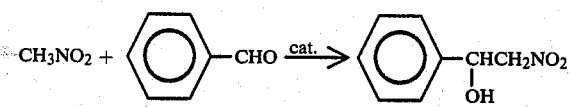

In Example 16, 0.87 g (8.2 mmol) benzaldehyde, 0.50 g (8.2 mmol) nitromethane, and 50 mg Rh(PMe₃)₃)Cl were contacted and reacted in a sealed tube overnight at 60°. At the end of this period, IR and ¹H-NMR analysis indicated approximately 50% conversion of starting materials to product.

In Example 17, 30 mg Rh(dmpe)₂Cl were added to a solution of 1.0 g (9.4 mmol) benzaldehyde and 0.57 g (9.3 mmol) nitromethane. An immediate exothermic reaction resulted, and a yellow solution formed. IR analysis immediately after mixing of reactants indicated approximately 40% conversion of reactants to product. The reaction was permitted to continue for approximately 18 hours, and during this period the reaction mixture turned red in color. IR analysis at this point indicated approximately 74% conversion of reactants to product. No traces of dehydration product were observed. Comparison of IR traces taken from the sample allowed to react overnight with those taken from a sample of the reaction mixture after two hours indicated that the reaction was largely complete after two hours.

EXAMPLE 18 AND COMPARATIVE EXPERIMENT C

Reaction of Benzaldehyde and 2-Nitroethanol to Produce 1,3-Dihydroxy-2-Nitro-1-phenylpropane

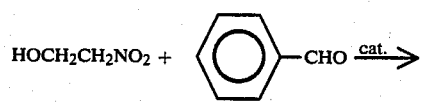

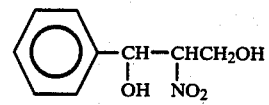

In Example 18, 1 g (9.4 mmol) benzaldehyde and 0.86 g (9.4 mmol) 2-nitroethanol were combined and 35 mg Rh(dmpe)₂Cl added to form a reaction mixture. The resulting reaction was slightly exothermic, and was stirred at about 23° for about 72 hours. IR analysis after one hour and after 72 hr indicated 54% conversion of reactants to product, suggesting the possibility of catalyst deactivation.

In Comparative Experiment C, the foregoing reaction was substantially repeated, except no catalyst was added. IR analysis after 72 hours indicated that no reaction had taken place.

EXAMPLE 19

Reaction of 3-Pyridine Carboxaldehyde and Nitromethane to Produce α-(Nitromethyl)-3-pyridinemethanol

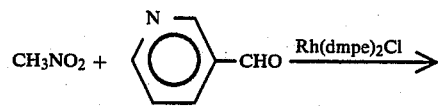

0.878 g (8.2 mmol) 3-pyridine carboxaldehyde, 0.5 g (8.2 mmol) nitromethane, and 40 mg Rh(dmpe)₂Cl were contacted and reacted in a stirred vessel in a N₂ dry box at 23°. After 2 hours, IR and ¹H-NMR analyses indicated greater than 90% conversion of reactants to product.

EXAMPLE 20

Reaction of 2-Nitropropane and Acetaldehyde to Produce 2-Methyl-2-Nitro-3-Hydroxybutane

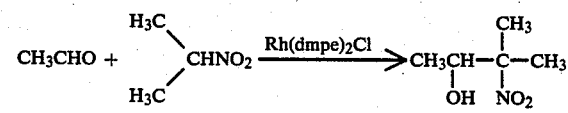

In a N₂ dry box, a 24 mL vial was charged with 0.49 g (11.11 mmol) acetaldehyde, 1.0 g (11.2 mmol) 2-nitropropane, and 40 mg Rh(dmpe)₂Cl. The resulting reaction mixture was stirred at about 23° for approximately 18 hours. At the end of this period, IR analysis indicated greater than 90% conversion of reactants to product 2-methyl-2-nitro-3-hydroxybutane.

EXAMPLES 21-24

Reaction of Paraformaldehyde and Nitromethane to Produce 2-(Hydroxymethyl)-2-Nitro-1,3-Propanediol and 2-Nitro-1,3-Propanediol

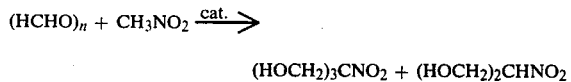

In Example 21, 1.0 g (16.4 mmol) nitromethane, 0.5 g (16.6 mmol) paraformaldehyde, and 50 mg $Rh(PMe_3)_3Cl$ were combined to form a reaction mixture, which subsequently polymerized. The polymeric material resulting was dissolved in chloroform and analyzed by GC. The analysis indicated that no reaction had occurred.

In Example 22, 0.5 g (8.2 mmol) nitromethane, 0.25 g (8.3 mmol) paraformaldehyde, and 50 mg $Pd(PMe_3)_4$ were combined in a 24 mL vial in a $N_2$ dry box and stirred for 5 minutes. Insoluble material was present, and chloroform was added to the reaction mixture. A yellow oil formed, and supernatant chloroform was separated by decantation. The yellow oil was washed again with chloroform, dissolved in acetone, dried over $MgSO_4$, and then excess acetone was removed by a stream of $N_2$. The resulting yellow residue was briefly dried under vacuum and analyzed by IR and $^1$H-NMR. This analysis indicated that the residue consisted of about 73% $(HOCH_2)_3CNO_2$ and about 27% $(HOCH_2)_2CHNO_2$.

In Example 23, 0.5 g (8.2 mmol) nitromethane was dissolved in 3 mL benzene, to which 0.24 g (8.0 mmol) paraformaldehyde and 50 mg $Pd(PMe_3)_4$ were added. The resulting reaction mixture was stirred at about 23° for about 18 hours. Analysis by $^1$H-NMR indicated greater than 90% conversion of reactants to $(HOCH_2)_3CNO_2$, based upon the starting quantity of paraformaldehyde.

In Example 24, 0.5 g (8.2 mmol) nitromethane, 0.24 g (8.0 mmol) paraformaldehyde, and 50 mg $Rh(dmpe)_2Cl$ were reacted substantially according to the procedure described in Example 23. $^1$H-NMR indicated a greater than 90% conversion of reactants to $(HOCH_2)_3CNO_2$, based upon the starting quantity of paraformaldehyde.

EXAMPLES 25-28 AND COMPARATIVE EXPERIMENTS E-J

Reaction of Allyl Cyanide and Acetaldehyde to Produce 2-(1-Hydroxyethyl)-2-Butenenitrile

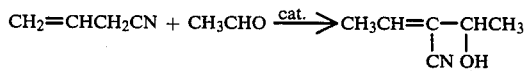

In Example 25, 50 mg $Rh(PMe_3)_3Cl$ were dissolved in 1 g allyl cyanide in a 24 mL vial. 1 mL acetaldehyde was added, the vial capped, and the resulting reaction mixture heated, with stirring, for about 18 hours at 60°. The vial was then opened and heated at 60° for an additional 15 minutes to remove excess acetaldehyde. The resulting solution was analyzed by GC, which indicated formation of 2(1-hydroxyethyl)-2-butenenitrile. In a separate experiment conducted substantially similarly, products were quantitatively analyzed by GC, which indicated formation of cis and trans isomers of 2(1-hydroxyethyl)-2-butenenitrile in 71% yield, and formation of 3-cyano-1,3-pentadiene in 5% yield, based upon the starting quantity of allyl cyanide. The reaction mixture was distilled at 0.15 mm Hg, and fractions were collected with b.p. 74°-80°, 80°-85°, and 85°-90°, each of which consisted of mixtures of cis and trans isomers of 2(1-hydroxyethyl)-2-butenenitrile by $^1$H-NMR, IR, and GC.

$^1$H-NMR (CDCl$_3$) δppm:

Isomer A (probably cis): 1.43 (d, J=7 Hz, 3H, CH3C—O); 2.03 (d, J=7 Hz, 3H, CH3C≡); 2.77 (broad s, 1H, OH); 4.40 (q, J=6.7 Hz, CH—O); 6.46 (q, J=7 Hz, CH≡).

Isomer B (probably trans): 1.43 (d, J=6.7 Hz, 3H, CH3C—O); 1.93 (d, J=7 Hz, 3H, CH3C≡); 2.77 (broad s, 1H, OH); 4.77 (q, J=7 Hz, 1H, CH—O); 6.46 (q, J=7 Hz, 1H, CH≡).

IR (neat): 3420 (vs, broad; OH); 2233 (s, CN); 1640 (m, C≡C).

Examples 26-28 and Comparative Experiments E-J were conducted substantially similarly to Example 25, except different catalysts were employed.

The $Rh(AsMe_3)_3Cl$ catalyst employed in Example 27 was prepared as follows. 1.9 g (15.8 mmol) trimethylarsine was dissolved in 5 mL cold tetrahydrofuran. The resulting solution was added dropwise to a solution of 1.0 g (2.6 mmol) $Rh_2Cl_2(C_2H_4)_4$, prepared as disclosed by Cramer, R., *Inorg. Chem.* 1:722 (1962), in 25 mL tetrahydrofuran. After 72 hours, solvent was removed by evaporation, leaving 2.15 g of a red-orange solid. Recrystallization of this material from toluene with pentane provided 1.90 g (3.8 mmol; 73%) of product $Rh(AsMe_3)_3Cl$, which was obtained as a light rust-brown colored crystalline solid.

Anal. Calcd. for $C_9H_{27}ClAs_3Rh$: C, 21.69; H, 5.46. Found: C, 21.83; H, 5.27.

TABLE IV

| Example/ Comparative Experiment | Catalyst | Product Yield (%) | Products Other Than 2-OH—3-Cy—3-Pentene |
|---|---|---|---|
| 26 | $Rh(PMe_3)_2PPh_3Cl$ | 69 | $CH_3CH=CHCH_2CN$ (8%) |
| 27 | $Rh(AsMe_3)_3Cl$ | 75 | $CH_3CH=CHCH_2CN$ (8%) |
| 28 | $Rh(dmpe)_2Cl$ | 90 | |
| E | none | 0 | |
| F | $Rh(PPh_3)_3Cl$ | 0 | |
| G | $Rh(AcAc)(C_2H_4)_2$ | 0 | |
| H | $[Rh(C_2H_4)_2Cl]_2$ | 0 | |
| I | $Rh[P(OMe)_3]_3Cl$ | 0 | |
| J | $Rh(CO)(PMe_3)_2Cl$ | 0 | |

EXAMPLES 29-32 AND COMPARATIVE EXPERIMENTS K AND L

Reaction of 3-Pentenenitrile and Acetaldehyde to Produce 2(1-hydroxyethyl)-3-pentenenitrile

In Example 29, 1 g 3-pentenitrile, 1 mL acetaldehyde, and 50 mg $Rh(PMe_3)_3Cl$ were contacted and reacted overnight at 60°. Analysis by GC indicated formation of 2(1-hydroxyethyl)-3-pentenenitrile in 90% yield. Distillation of the resulting product mixture at 0.3 mm Hg yielded fractions boiling at 79°–82°, 83°–84°, and 85°–89°, each of which consisted of mixtures of cis and trans isomers of 2(1-hydroxyethyl)-3-pentenenitrile.

$^1$H-NMR (CDCl$_3$): δppm 1.33 (d, J=7 Hz, 3H, CH$_3$C—O); 1.77 (d, J=7 Hz, 3H, CH$_3$C=); 1.93 (s, 1H, OH); 3.30 (q, J=7 Hz, 1H, CHCN); 3.93 (q, J=7 Hz, 1H, CHOH); 5.27–5.51 (m, 1H, CH=); 5.73–6.13 (m, 1H, CH=).

IR (neat): 3425 (vs, broad, OH); 2223 (m, CN); 1668 (m, C=C).

Examples 30–32 and Comparative Experiments K and L were conducted substantially similarly to Example 29, except for variations in catalyst. The results obtained are set forth in Table V, below:

TABLE V

| Example/Comparative Experiment | Catalyst | Product Yield (%) |
|---|---|---|
| 30 | Rh(PMe$_3$)$_3$Cl | 90 |
| 31 | Rh(PMe$_3$)$_2$PPh$_3$Cl | 3 |
| 32 | Rh(AsMe$_3$)$_3$Cl | 26 |
| K | None | 0 |
| L | Rh(PPh$_3$)$_3$Cl | 0 |

EXAMPLE 33

Reaction of Benzaldehyde and Allyl Cyanide to Produce
α-Ethylidene-β-Hydroxybenzenepropanenitrile

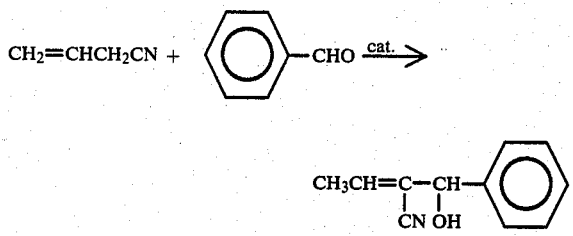

1 g (9.4 mmol) benzaldehyde, 1 g (14.9 mmol) allyl cyanide, and 50 mg Rh(PMe$_3$)$_3$Cl were reacted overnight at 60°, with stirring, in a sealed vial. At the end of this reaction period, the vial was opened and held at 60° for an additional 15 minutes. GC and IR analysis of the reaction mixture indicated approximately 20% conversion of reactants to product.

EXAMPLE 34

Reaction of Malononitrile and Acetaldehyde to Produce Ethylidenepropanenitrile and
(1-Hydroxyethyl)propanedinitrile

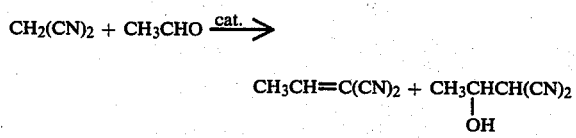

1 g (15.1 mmol) malononitrile, 0.8 g (18.2 mmol) acetaldehyde, and 25 mg Rh(PMe$_3$)$_3$Cl were reacted overnight at about 23° in a sealed vial, with stirring. Water was observed to form in the reaction mixture. $^1$H-NMR of the resulting product mixture indicated approximately 35% conversion of reactants to ethylidenepropanenitrile and 15% conversion of reactants to (1-hydroxyethyl)propanenitrile.

What is claimed is:

1. A catalytic process for preparing nitroalcohols or cyanohydrins, comprising reacting an aldehyde compound or group of the formula $$RCHO \qquad (I)$$

with a compound or group of the formula

in the presence of a catalytic amount of a low-valent transition metal complex selected from the group consisting of (a)

(b)

(c)

(d) precursors which are converted to complexes of formulas IV, V, or VI during the process;
wherein
A is a phosphine or arsine ligand moiety having a ligand cone angle θ which is less than or equal to 132°, selected from the group consisting of

mixtures thereof;
B is an olefin, or a phosphine or arsine ligand moiety A', defined as A, above, except that θ can be greater than 132°;
E is P or As;
M$^1$ is Co(I), Rh(I), or Ir(I);
M$^2$ is Ni(I), Pd(O), or Pt(O);
M$^3$ is Fe(O), Ru(O), or Os(O);
R is H, alkyl, substituted alkyl, aryl, substituted aryl, aralkyl, substituted aralkyl, alkaryl, substituted alkaryl, or heterocyclic;
R$^1$, R$^2$, and R$^4$ are, independently, F, NO$_2$, COR, COOR, CN, or R;
R$^3$ is F, NO$_2$, CN, or RCH=CH;
R$^5$, R$^6$, R$^7$, R$^8$, R$^9$, R$^{10}$ and R$_{11}$ are, independently, H, lower alkyl, or lower aryl;
X is an anion;
j is 2, 3, or 4;
k, m, and t are independently 0 or 1;
n is 2, 3, 4, or 5;
p is 1, 2, or 3; and
s is 3, 4, or 5;

provided that the sum of m and n is less than or equal to 5; the sum of j and k is less than or equal to 4; and the sum of s and t is less than or equal to 5.

2. A process according to claim 1, wherein the catalyst complex is $M^1A_nB_mX$, wherein $M^1$, A, B, X, m, and n are as defined in claim 1.

3. A process according to claim 2, wherein A is $ER^5R^6R^7$, E is P, and $R^5$, $R^6$, and $R^7$ are as defined in claim 1.

4. A process according to claim 3, wherein $R^5$, $R^6$, and $R^7$ are each methyl, ethyl, isopropyl, or isobutyl groups.

5. A process according to claim 3, wherein $R^5$ is hydrogen, $R^6$ is phenyl, and $R^7$ is hydrogen or phenyl.

6. A process according to claim 2, wherein A is $[R^8R^9E^9(CH_2)_pER^{10}R^{11}]/2$, E is P, and $R^8$, $R^9$, $R^{10}$, $R^{11}$, and p are as defined in claim 1.

7. A process according to claim 6, wherein the catalyst complex is selected from the group consisting of $M^1(dmpe)_2X$, $M^1(depe)_2X$, $M^1(dppm)_2X$, $M^1(dppe)_2X$, and $M^1(dppp)_2X$.

8. A process according to claim 7, wherein the catalyst complex is $M^1(dmpe)_2X$.

9. A process according to claim 1, comprising reacting an aldehyde compound or group of the formula

RCHO           (I)

with a nitro compound or group of the formula

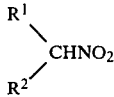
(II)

to produce a nitroalcohol of the formula

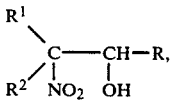

wherein R, $R^1$, and $R^2$ are as defined in claim 1.

10. A process according to claim 9, wherein R1 and R2 are independently H, F, lower alkyl, substituted lower alkyl, lower aryl, substituted lower aryl, or CN.

11. A process according to claim 10, wherein $R^1$ and $R^2$ are independently H, F, lower alkyl, or substituted lower alkyl.

12. A process according to claim 1, comprising reacting an aldehyde compound or group of the formula

RCHO           (I)

with a nitrile compound or group of the formula

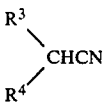
(III)

to produce a cyanohydrin of the formula

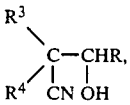

wherein R, $R^3$, and $R^4$ are as defined in claim 1.

13. A process according to claim 12, wherein $R^3$ is CN or RCH=CH, $R^4$ is R, and R is lower alkyl, substituted lower alkyl, aryl, or substituted lower aryl.

* * * * *

UNITED STATES PATENT AND TRADEMARK OFFICE
CERTIFICATE OF CORRECTION

PATENT NO. : 4,581,178
DATED : April 8, 1986
INVENTOR(S) : David Milstein

It is certified that error appears in the above—identified patent and that said Letters Patent is hereby corrected as shown below:

Column 14, line 52, "Ni(I)" should be --Ni(O)--.

Signed and Sealed this

Thirtieth Day of December, 1986

Attest:

DONALD J. QUIGG

Attesting Officer     Commissioner of Patents and Trademarks